United States Patent
Mitsuyama et al.

[19]

[11] Patent Number: 5,911,002
[45] Date of Patent: *Jun. 8, 1999

[54] PATTERN RECOGNITION SYSTEM

[75] Inventors: Satoshi Mitsuyama, Tokyo; Jun Motoike, Hachioji; Norio Oowada, Ibaraki-ken; Yasuaki Kojima, Hitachinaka, all of Japan

[73] Assignee: Hitachi, Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/715,592

[22] Filed: Sep. 18, 1996

[30] Foreign Application Priority Data

Sep. 27, 1995 [JP] Japan ................... 7-249082

[51] Int. Cl.$^6$ ................... G06K 9/62; G06E 1/00
[52] U.S. Cl. ................... 382/158; 382/156; 382/159; 395/21
[58] Field of Search ................... 382/158, 157, 382/156, 159, 224; 395/21–24

[56] References Cited

U.S. PATENT DOCUMENTS

| 4,965,725 | 10/1990 | Rutenberg ................... 382/155 |
| 5,088,816 | 2/1992 | Tomioka et al. ................... 356/39 |
| 5,335,291 | 8/1994 | Kramer et al. ................... 395/21 |

FOREIGN PATENT DOCUMENTS

| 57-500995 | 6/1982 | Japan | G01N 15/07 |
| 58-29872 | 6/1983 | Japan | G01N 33/48 |
| 63-94156 | 4/1988 | Japan | G01N 33/48 |
| 1-119765 | 5/1989 | Japan | G01N 33/48 |
| 3-131756 | 6/1991 | Japan | G01N 33/49 |
| 4-1870 | 1/1992 | Japan | G06F 15/70 |
| 4001870A | 1/1992 | Japan | G06F 15/70 |
| 4-294444 | 10/1992 | Japan | G06F 15/18 |
| 5-296915 | 11/1993 | Japan | G01N 15/14 |

OTHER PUBLICATIONS

"Neural Network Information Processing" issued from Sangyo–Tosho publisher, 1988, pp. 50–54.

*Primary Examiner*—Jose L. Couso
*Assistant Examiner*—Duy M. Dang
*Attorney, Agent, or Firm*—Fay, Sharpe, Beall, Fagan, Minnich & McKee

[57] ABSTRACT

In a pattern recognition system provided with a pattern recognition processing unit having a network structure constructed of an input layer for inputting a feature parameter of a subject under recognition as input information an intermediate layer for processing the input information and an output layer for outputting a processed result output values of respective output nodes for constituting the output layer, corresponding to the input information, are compared with each other by the pattern recognition processing unit, and a classification item corresponding to the output node whose output value is maximum is stored into a storage unit as a recognized result with respect to the input information. The pattern recognition system is also provided with a reliability evaluating unit for setting a threshold with respect to an output value of each of the output nodes and for evaluating reliability of the recognized result based upon the output values of the respective output nodes. When the reliability evaluating unit judges that the reliability is high, the recognized result is stored into the storage unit.

11 Claims, 6 Drawing Sheets

PATTERN RECOGNITION SYSTEM

BACKGROUND OF THE INVENTION

The present invention generally relates to a pattern recognition technique, namely to a pattern recognition system capable of rejecting an object difficult to be pattern-recognized without performing a pattern recognition in the case that this object difficult to be pattern-recognized appears, and the reliability of pattern-recognizing results is low. More specifically, the present invention is directed to a pattern recognition system suitable for a urinary sediment analyzer capable of classifying particles contained in urine.

A urinary sediment examination is such an examination that solid components such as blood cells and epithelial cells contained in urine are investigated, and then sorts and amounts of the respective solid components are reported. Conventionally, this urinary sediment examination has been carried out in the following manner. That is, a predetermined amount of urine is centrifuged to acquire sediment components, these sediment components are stained, and then the stained sediment components are collected as a sample on a smear preparation. Thereafter, a technician observes this sample by using a microscope. The respective components are classified based upon features such as a shape and stainability. Since even same components show various shapes, there is much possibility that the classification of these components becomes difficult. Also, since a urine sample is continuously exposed to the open air after it has been acquired, there are some cases that contamination existing in air enters into the urine sample. As to such subjects, the technician does not classify these contaminants, but may classify and count only typical subjects which can be correctly classified.

The techniques capable of automatically executing the urinary sediment examination are disclosed in, for instance, JP-A-57-500995 (WO81/03224), JP-A-63-94156, and JP-A-5-296915, in which solid components, or particles contained in the urine are photographed as still images. In these conventional techniques, the sample is supplied to pass through the flow cell having the specific shapes, and the particles contained in the sample are supplied to flow into the wide photographing region. When the solid components are detected within the sample, the flash lamp is turned ON, so that the enlarged images of the solid components contained in the urine are photographed as the still images. To automatically analyze the sediment components photographed as the still images, first of all, after the region of the sediment components is segmented from the background region thereof on the image, the image feature parameters in the region of the sediment components are calculated. The classification is carried out based on these feature parameters. As the image feature parameters, an area, a perimeter, and a mean color density are employed. On the other hand, as the technique for segmenting the region of the solid component from the background region on the image, there is described in, for example, JP-A-1-119765 entitled "REGION SEGMENTING METHOD OF BLOOD CELL IMAGE". In this technique, the image region is segmented in the color space by employing the threshold calculated from the gray level histogram.

As the technique for classifying a subject from an image feature parameter, for example, JP-A-58-29872 and JP-A-3-131756 describe the classification of the blood cell image. JP-A-58-29872 describes that either the discrimination theory which is combined by the statistical discrimination function in the multiple stage based on the image feature parameters or the decision tree theory is employed. JP-A-3-131756 describes that the multi-layer network is employed as the recognition theory. When the pattern recognition is carried out by utilizing the network structure, the following methods are normally used. First, the output nodes whose quantity is equal to that of the classes in which subjects are to be classified are prepared, and then these output nodes are allocated to these classes one by one. Next, the network is constructed by employing the training pattern in such a manner that when a certain pattern is entered, the output of the output node corresponding to the class belonging to the input pattern, among the outputs from the respective output nodes, becomes maximum. When an unknown pattern is actually recognized, the unknown pattern is inputted. Assuming now that the class corresponding to the output node for outputting the maximum value among the output values of the respective output nodes is recognized as the class belonging to the unknown pattern, this class is displayed as the recognized result. JP-A-3-131756 further describes that the threshold is provided to the output value, and when the maximum output value is smaller than, or equal to this threshold, the sample cannot be classified. Also, JP-A-4-1870 describes that the confirmation degree is compared with the threshold; when the confirmation degree is greater than the threshold, the output result is used as the recognized result, whereas when the confirmation degree is smaller than the threshold, the output result is rejected. As a consequence, the reliability of the recognized result can be increased JP-A-4-294444 describes that the output reliability of the neural network is evaluated by the reliability evaluating means.

SUMMARY OF THE INVENTION

However, as described above, it is difficult to perform the correct classification in the urinary sediment examination. Also, there are many components which are necessarily not classified by the technician. These difficult classified subjects may cause problems in the construction of the examination system. For instance, as explained above, in the examination system such that the sediment components are photographed as the image and recognized, when a predetermined amount of urine is used as a sample, in such a case that a large number of sediment components are present, all of the appearing subjects could not be processed due to the hardware restrictions, for instance, the image processing speed, the image data transfer speed, and the storage capacities of the image memory and the storage device. Under such a circumstance, when a very large number of components are present which are not classified, there is a risk that the components which should be originally classified are overlooked, thus classifications results in deterioration of the statistical reliability.

The present invention has been made to solve the above-described problems, and has an object to provide such a pattern recognition apparatus. That is, in this pattern recognition apparatus, when a component appears which need not be classified, this component is detected at an initial processing stage of a pattern recognition process. The subsequent processing stages are omitted in order to avoid overlooking of a component which should be originally classified, so that statistical reliability is secured.

Normally, when a network is constructed (learning), a learning pattern to be classified is prepared. When a certain pattern is inputted, such target output is applied that the output of the output node corresponding to the class belonging to the input pattern becomes 1, and other output nodes become 0 among the outputs of the respective output nodes.

Then, this network is constituted in such a way that the value approximated to the teacher data is outputted. When an unknown pattern is inputted, such a class corresponding to the output node for outputting the maximum value among the respective output nodes is recognized as the pattern recognized result (simply, referred to as a "recognized result" hereinafter). At this time, it is conceivable that such an input pattern is approximated to the learning pattern. That is, the combination of the output values derived from the respective output nodes is approximated to the combination of the values given as the teacher data (only one output node outputs 1, and other output nodes output 0). Conversely, when the combination of the output values of the output nodes is greatly different from the combination of the values given as the teacher data, the input pattern is greatly different from the learning pattern. Thus, there is great possibility that these components need not be classified, or could be difficultly classified. Even when the recognition is carried out, the reliability thereof becomes low. For instance, the reliability of recognition is low when the maximum value becomes a relatively small value, or when the output values other than the maximum output values become relatively large values.

As a consequence, such a means is employed that thresholds are set to the respective output values of these output nodes in the network structure, and reliability of recognition is evaluated based on the respective output values of the output nodes. Only when the reliability is high, the recognized result is outputted to perform the process operation at the post stage. When the reliability is low, the recognized result is not outputted, and no further process operation at the post stage is carried out. Otherwise, when a plurality of preselected specific output nodes output maximum values, the recognized result is stored into the storage device. In another system into which a subject under classification is inputted as an image, when it is difficult to recognize too small a subject due to resolution of the imaging system, an area of this small subject, a perimeter thereof, and projection lengths along the X-axis and the Y-axis on the image are calculated. Then, no recognition is carried out as to such a subject having a dimension smaller than, or equal to a preset dimension.

In other words, a pattern recognition system according to the present invention is featured as follows:

In a pattern recognition system comprising pattern recognition processing means having a network structure constructed of: an input layer for inputting a feature parameter of a subject under recognition as input information; an intermediate layer for processing said input information; and an output layer for outputting a processed result; in which output values of respective output nodes for constituting said output layer, corresponding to said input information, are compared with each other by said pattern recognition processing means, and a class corresponding to said output node whose output value is maximum is stored into storage means as a recognized result with respect to said input information, (1) said pattern recognition system further comprises: reliability evaluating means for setting a threshold with respect to an output value of each of said output nodes and for evaluating reliability of said recognized result based upon the output values of said respective output nodes; and when said reliability evaluating means judges that the reliability is high, said recognized result is stored into said storage means; and (2) when a plurality of predetermined specific output nodes output maximum values, the recognized result is stored in the storage means.

In accordance with the present invention, such a subject is detected which can be hardly recognized/classified and the recognition reliability of which is low even when the automatic pattern recognition is carried out. This subject can be eliminated from the process stages, so that the efficiency of the process stages can be increased, and the storage capacity of the storage device can be saved.

Referring now to FIG. 1, the present invention is summarized as follows. According to the present invention, the feature parameter of the subject under recognition is calculated (S6). While giving an attention to the dimension among the feature parameters, such a subject having a very small dimension is eliminated from the process operation (S7). Furthermore, parameters indicative of recognition reliability are obtained with reference to the output values of the respective output nodes of the neural network. These parameters are compared with the thresholds used to evaluate the reliability. When the reliability is low, this subject is eliminated from the recognition/classification (S8, S9). As a consequence, in the pattern recognition, a detection can be made of such subjects which can be hardly recognized/classified, and which are eliminated from the recognition by the technician. Then, the other subjects can be recognized and classified.

BRIEF DESCRIPTION OF THE DRAWINGS

The invention may be best understood from a detailed description to be read in conjunction with the accompanying drawings, in a which.

DESCRIPTION OF THE PREFERRED EMBODIMENTS

Referring now to drawings, a urinary sediment analyzer will be described in detail as an embodiment of a pattern recognition system according to the present invention.

Figure 6:
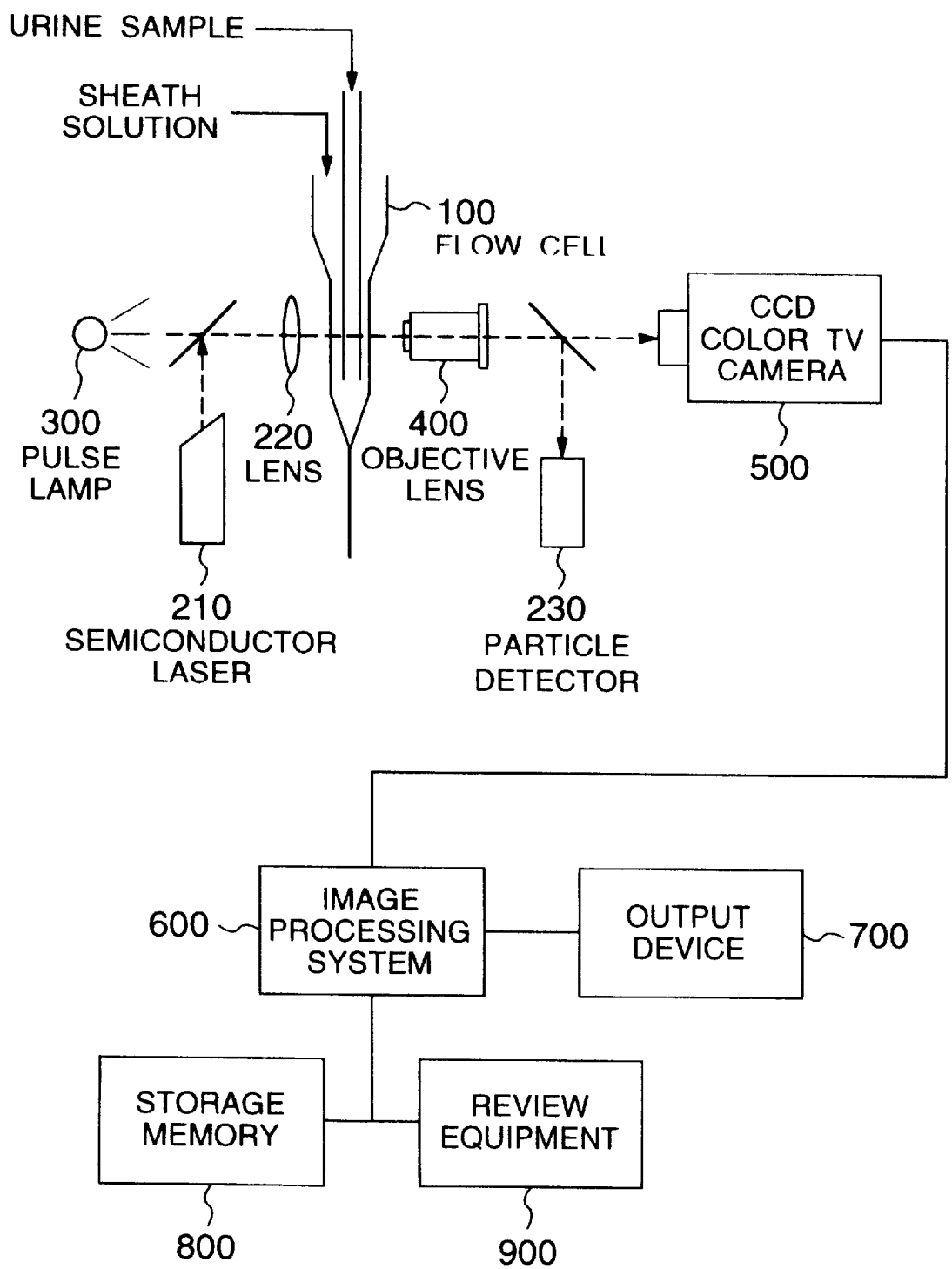
FIG. 6 schematically represents a structural example of the urinary sediment analyzer corresponding to the pattern recondition system according to an embodiment of the present invention.

FIG. 6 schematically indicates a structural example of a urinary sediment analyzer corresponding to a pattern recognition system according to one embodiment of the present invention. This drawing shows a system arrangement containing an imaging system and a recognition system of the urinary sediment analyzer. In this urinary sediment analyzer, a flow cell 100 is employed to thereby form a flat flow of a urine sample. This sample flow is made thin as to a thickness thereof, and wide as to a widthness thereof between a CCD color television camera 500 and a pulse lamp 300. Laser light is irradiated from a semiconductor laser 210 via a lens 220 to the urine sample flow formed within the flow cell 100 through which a sheath solution is rendered to flow, so that a particle detector 230 detects that solid components pass through the flow cell 100. In synchronism with this detection signal, light emitted from the pulse lamp 300 is irradiated to the urine sample flow. Since the light of the pulse lamp 300 is instantaneously irradiated, an image of the solid components contained in the urine, which is enlarged by way of an objective lens 400, may be photographed as a still image by using the CCD color television camera 500. This analyzer owns a plurality of measurement modes, and changes a rate of flow and a velocity of flow about the sample flowing through the flow cell 100, and also magnifying power of the objective lens 400.

The acquired image is transferred to an image processing system 600. This image processing system 600 determines the sort of the solid components existing in the image, and counts the number of subjects of each sort in a single sample under examination. The count result is notified via an output device 700 to an operator A printer is used as the output device 700. Both the image data and the recognition result about this image are transferred from the image processing system 600 to a storage memory 800 (with employment of a hard disk apparatus).

Figure 2:
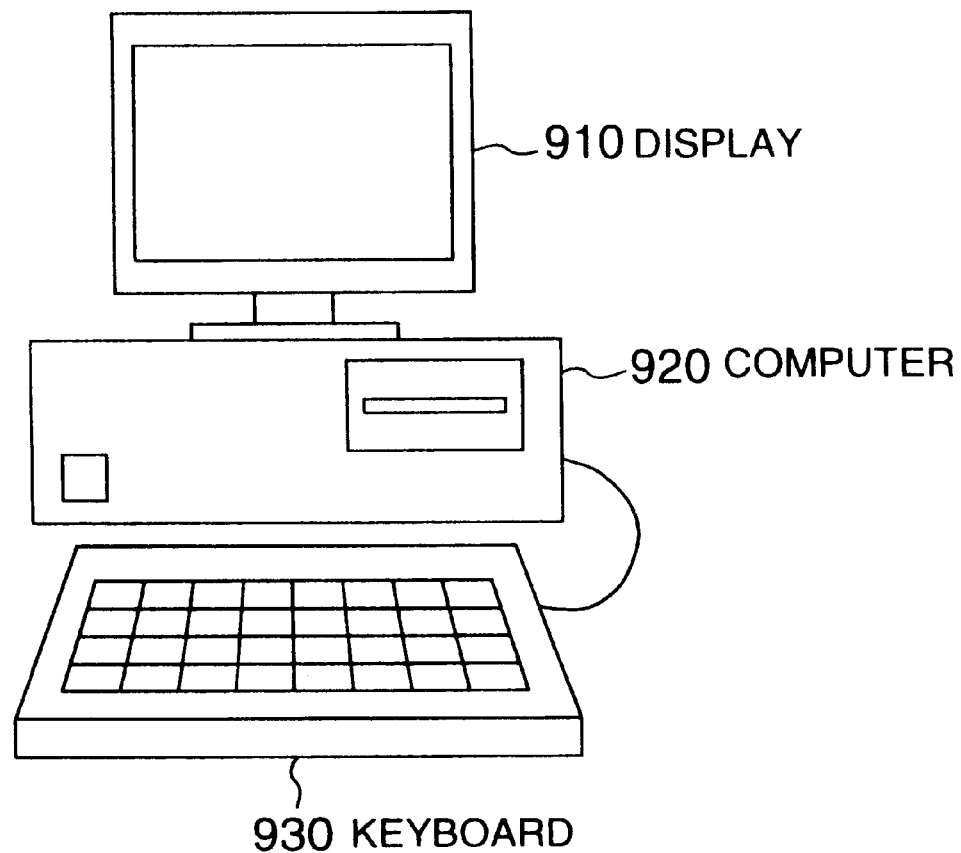
FIG. 2 schematically illustrates a structural example of a review equipment according to an embodiment of the present invention.

FIG. 2 schematically shows a structural example of a review equipment according to an embodiment of the present invention. As indicated in FIG. 2, the review apparatus 900 may display an image and a recognition result stored in the storage memory 800 by employing a computer 920 equipped with a CRT display 910 and a keyboard 930, if required. Also, when the recognition result displayed on the CRT display 910 contains an error, an operator may correct this erroneous recognition result while observing the image displayed on the CRT display 910, and then may store again the corrected recognition result into the storage memory.

Figure 3:
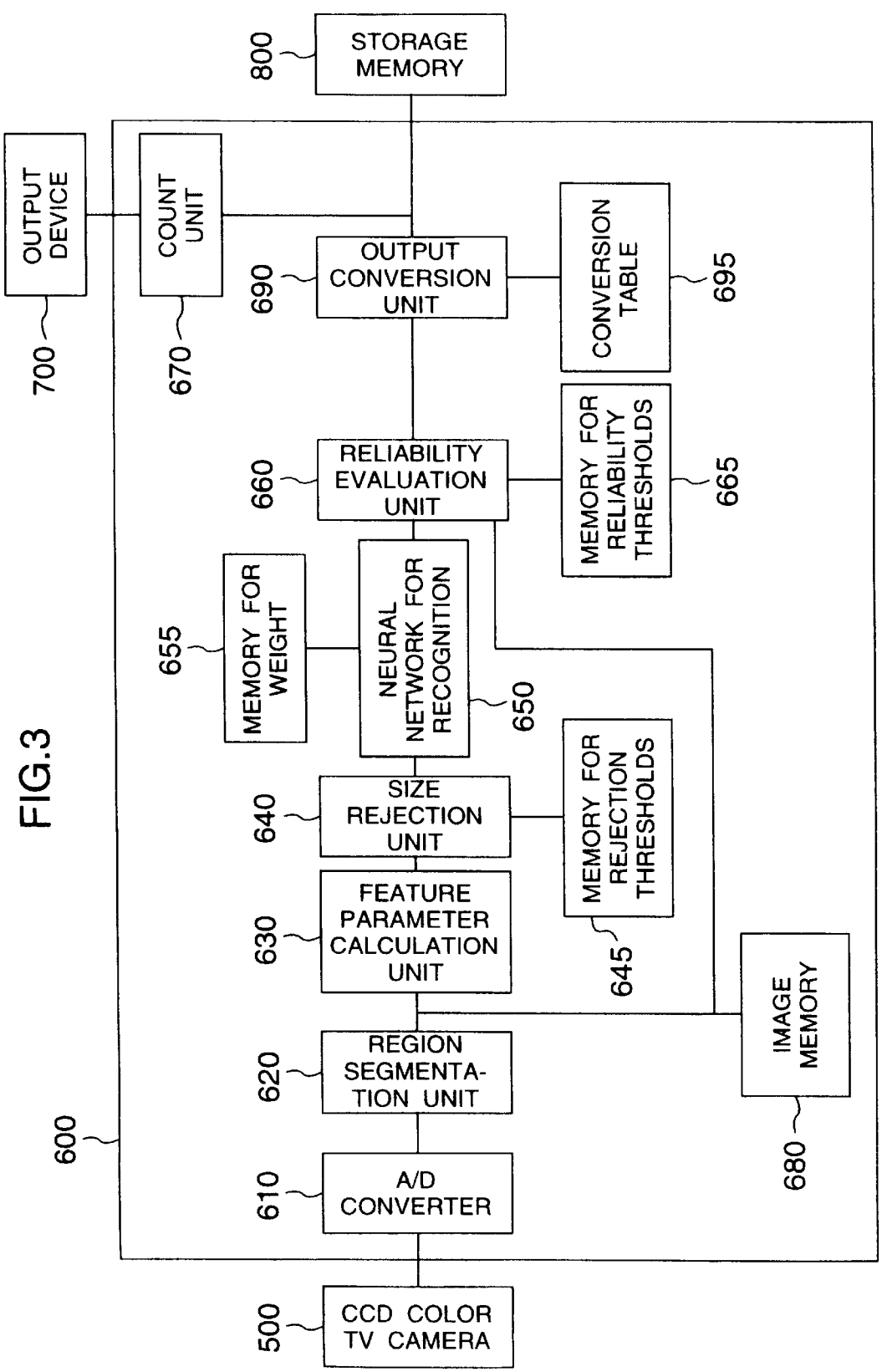
FIG. 3 schematically shows a structural example of an image processing system according to an embodiment of the present invention.
Figure 4:
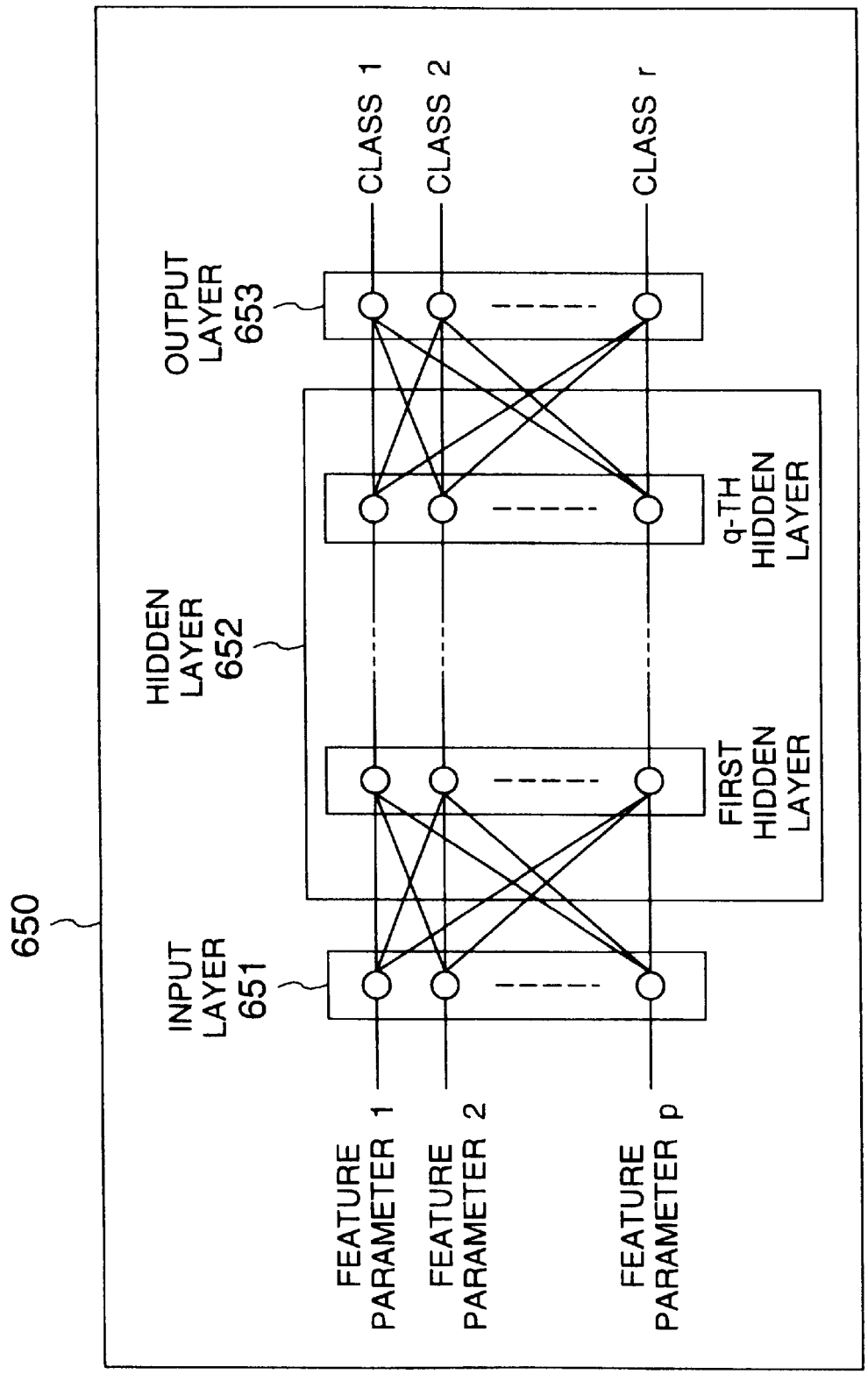
FIG. 4 schematically indicates a structural example of a neural network for recognition according to an embodiment of the present invention.
Figure 5:
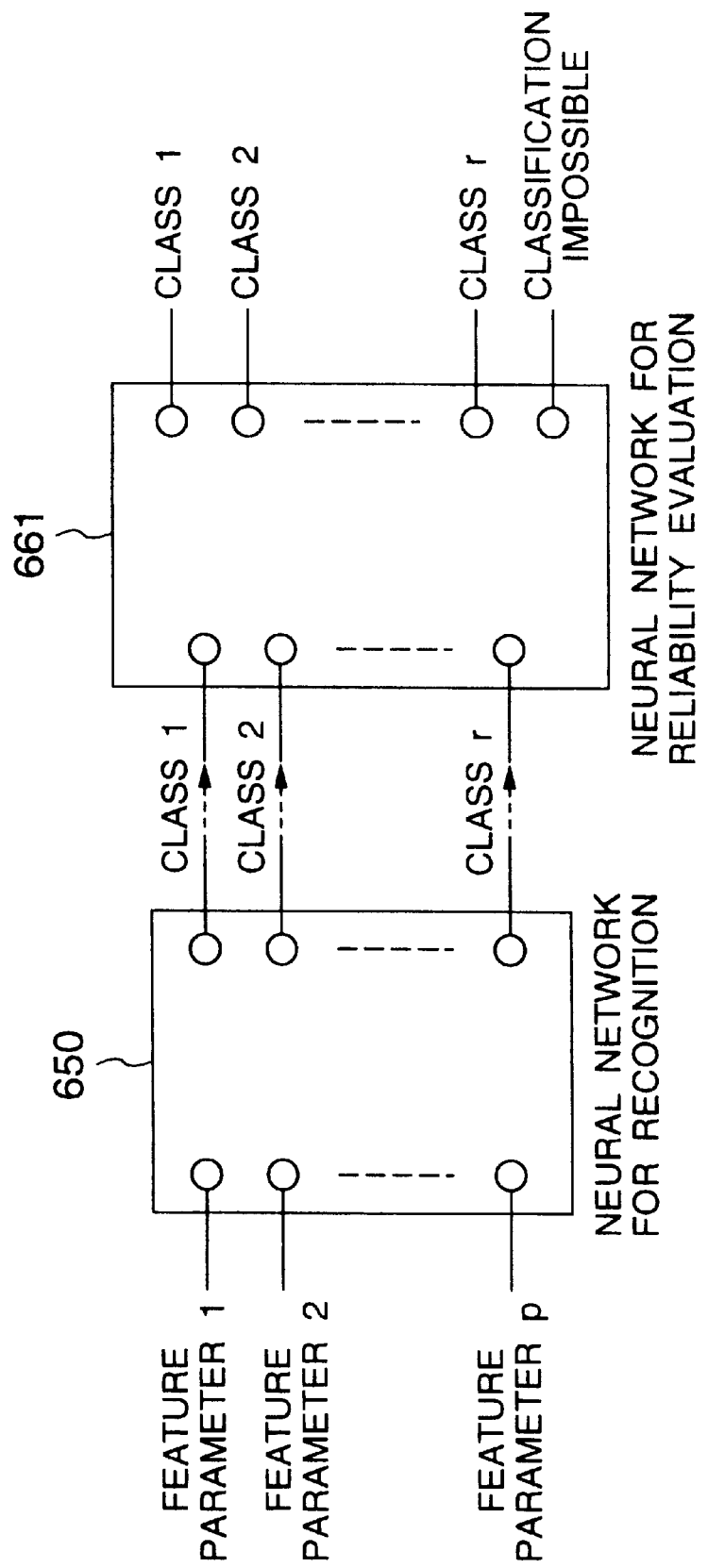
FIG. 5 schematically represents a connection relationship between the neural network and a neural network for reliability evaluation according to an embodiment of the present invention.

Next, a more detailed description will now be made of the internal arrangement of the image processing system 600. FIG. 3 schematically represents a structural example of the image processing system according to an embodiment mode of the present invention. FIG. 4 schematically shows a structural example of a neural network for recognition according to an embodiment mode of the present invention. FIG. 5 schematically indicates a connection relationship between the neural network for recognition and a neural network for reliability evaluation according to an embodiment mode of the present invention. An analog image signal inputted from the CCD color TV camera 500 is converted into digital image data by an A/D converter 610, and then the digital image data is sent to a region segmentation unit 620. The region (segmented) segmentation unit 620 segments an image into a background region and a subject region, and the image data of every segmented subject is stored into an image memory 680. A feature parameter calculation unit 630 calculates a feature parameter of the segmented region as the subject region by the region segmentation unit 620. In the case that a plurality of subject regions are present in the image, the feature parameters as to these subject regions are calculated respectively. As to the feature parameters, the following items are utilized, for example, an area of a subject region, a perimeter thereof, a projection length thereof on the image along the X-axis direction, another projection length thereof thereon along the Y-axis direction, and mean color density.

In a size rejection unit 640, a feature parameter related to a dimension of the subject region among the obtained feature parameters is employed, and a process operation subsequent to the recognition process by the neural network in a post stage is omitted as to such a region smaller than a predetermined size. Since it is difficult to correctly classify a subject having a small size due to the resolution of the CCD color TV camera 500 and the influences caused by the flow velocity of the sample, and further most of subjects which should be actually excluded from the recognition are very small components, the subsequent unnecessary process operations an be omitted by the size rejection unit 640. Also, since the enlarging magnification during the photographing operation and the flow velocity of the sample are different from each other in the measurement modes, the size rejection unit 640 must select and execute the proper process operation every time the measurement mode is selected.

A typical process operation by the size rejection unit will now be described as to such a case that assuming that the perimeter among the feature parameters of the subject region is selected to be "L", "L" is used to reject the size. As previously described, this system owns a plurality of measurement modes containing the different flow rates of the urine samples and the different magnifying power of the objective lens 400. In this case, the number of this measurement mode is assumed as "k". At this time, "k" pieces of values "$L_1$" to "$L_k$" have been stored in a memory 645 for rejection thresholds, and a selection is made of the values adapted to the measurement mode. In other words, when the system is under operation in the measurement mode "i", "Li" is selected as the threshold. Then, "Li" is compared with the perimeter of the subject region, and when L>Li, the feature parameter is transferred to the neural network 650 for recognition so as to be processed in the post stage. Assuming now that when L≦Li, this subject is rejected, no process operation in the post stage is carried out, and immediately, the process operation for the next subject is advanced.

It should be noted that although this example has described the employment of the perimeter of the subject, if a feature parameter indicates the dimension of the subject such as the area, the projection length along the X-axis direction, and the projection length along the Y-axis direction, then this feature parameter may be similarly employed. Alternatively, a plurality of feature parameters may be combined with each other and the combined feature parameter may be utilized. For instance, another case will now be explained in which the projection length along the X-axis direction is used in addition to the perimeter "L". It is now assumed that the projection length to the X-axis direction is "Px". At this time, while "2k" pieces of values $L_1$ to $P_{xk}$ are stored in the threshold memory, when the system is operated in the measurement mode "i", the process operation is carried out by employing Li and Pxi. When L>Li and Px>Pxi, process operations in the post stage are performed. In the case other than the above-mentioned cases, assuming now that this subject is rejected from the process operation, no process operation in the post stage is carried out, and the process operation for the next subject is immediately advanced.

The above explanation has been made of such cases that the same feature parameter is employed in the respective measurement modes. Alternatively, for instance, both the perimeter and the area may be employed in the measurement mode 1, and both the area and the projection length along the X-axis direction may be employed in the measurement mode 2. Namely, the different feature parameters may be used in the respective measurement modes, or the differently combined feature parameters may be used in every measurement modes. It should also be noted that although the thresholds to be used have been stored in the memory 645 for rejection thresholds, these thresholds may be rewritten by the user, if required. At this time, for example, the threshold is designated by employing the keyboard 930 of the review equipment 900, and the designated threshold value is transferred from the review equipment 900 to the memory 645 for rejection thresholds.

The feature parameter about the subject which has not been rejected by the size rejection unit is entered into the neural network 650 for recognition so as to be recognized therein. As illustrated in FIG. 4, the neural network 650 for recognition is arranged by an input layer 651, an output layer 653, and a plurality of hidden layer 652. In FIG. 4, there is shown the arrangement of the neural network having q layers of the hidden layers, which classifies the input parameter into r pieces of classes (classification items) by employing p pieces of feature parameters. The input layer 651 owns the same number of nodes as the feature parameters, and a specific feature parameter is inputted into each of the nodes. The output layer 653 owns the same number of classes to be classified (classification items), and the respective nodes correspond to the specific classes (classification items). In case of a urinary sediment analyzer, for example, there are red blood cells, white blood cells, and epithelial cells as the classes (classification items). The hidden layer 652 is constructed of either a single layer or plural layers, and each of these layers owns a plurality of nodes.

The input layer 651 outputs the inputted value to the respective nodes of the first layer of the intermediate layer 652. The respective nodes of the intermediate layer 652 input a weighted sum of the outputs from the respective nodes of the prestaged layers into the bounded monotone increasing function called as a "sigmoid function", and then output the value calculated based upon the sigmoid function as the output of the node. A calculation performed by the respective nodes of the intermediate layer 652 and the output layer 653 is expressed in (formula 1):

$$z = f(\Sigma w_i x_i - \theta) \quad (1)$$

It should be noted that symbol "z" indicates the output value to the succeeding layer, symbol "$x_i$" represents the output value of the i-th node of the preceding layer, symbol "$w_i$" shows a weighing value, symbol "$\theta$" denotes a threshold, symbol "f" represents the sigmoid function, and the summation "$\Sigma$" is carried out as to i=1 through i=n (symbol "n" being a quantity of nodes of preceding layer). An example of the sigmoid function is expressed n formula (2):

$$f(x) = 1/\{1 + \exp(-x)\} \quad (2)$$

The operation of the neural network is defined based upon the weighing value Wi and the threshold $\theta$ employed in each of the nodes. In this analyzer, the different weighing values Wi and the different thresholds $\theta$ from each other in the respective modes are stored in the memory 655 for weight, and the values for the respective modes are set to the neural network 650 for recognition during the operation.

The neural network 650 for recognition previously learns by employing learning data in every measurement mode. During the learning, the learning operation is performed in such a manner that a large number of data belonging to the respective classes (classification items) are prepared, and when the feature parameter of a certain image is inputted, the output of the node of the output layer 653 corresponding to the class (classification item) to which this image belongs becomes "1", whereas the outputs of other nodes of the output layer 653 become "0". For instance, the learning operation is carried out in such a way that the feature parameters 1 to p calculated from the images belonging to the class (classification item) 1 are inputted to the respective nodes of the input layer 651, and the output of the node corresponding to the class (classification item) 1 of the output layer 653 becomes "1", whereas the outputs of the odes corresponding to the classes (classification items) 2 to r become "0". As the learning method of the neural network, the back propagation method (described in, for instance, "NEURAL NETWORK INFORMATION PROCESSING" issued from SANGYO-TOSHO publisher, 1988, pages 50 to 54) may be utilized.

The output from the neural network 650 for recognition is sent to the reliability evaluation unit 660 of FIG. 3. The reliability evaluation unit 660 judges as to whether or not the reliability of the recognition result is high based upon any one of the below-mentioned methods (1) to (7). Only when it is judged that the reliability is high, the output values of the respective output nodes of the neural network 650 for recognition are transferred to the output conversion unit 690, the image data for the subject is read from the image memory 680, and then the read image data is stored into the storage memory 800. Alternatively, the operator may select any one of the below-mentioned methods (1) to (7). At this time, for instance, a selection is made by the operator by using the keyboard 930 of the review equipment 900. It should be noted that in the following neural network 650 for recognition, the class to be classified (classification item) corresponds to an r class (classification item), the output value of each output node of the output layer 653 of the neural network 650 for recognition is $Zi(1 \leq i \leq r)$, and the threshold with respect to the output value of each output node is $Si(1 \leq i \leq r)$. Furthermore, $Zi(1 \leq i \leq r)$ is sorted in the descent order, so that the output values of the output nodes are assumed as $Z_{h1}$ (maximum value, assuming $Z_a = Z_{h1}$), $Z_{h2}$ (second maximum value, assuming $Z_b = Z_{h2}$), $Z_{h3}$, - - - , $Z_{hr}$ (minimum value), to which the thresholds $Si(1 \leq i < r)$ with respect to the output values of the respective output nodes correspond to $S_{h1}, S_{h2}, S_{h3}, - - -, S_{hr}$. For example, when the sorted results in the descent order are equal to $Z_5$ (maximum value), $Z_3, Z_1, - - -$, h1=5, h2=3, h3=1, - - - , so that $Z_5$ (maximum value) is compared with $S_5$.

It is also assumed that the node corresponding to the class (classification item) a ($1 \leq a < r$) outputs the maximum value $Z_a$, and the node corresponding to the class (classification item) b ($1 \leq b \leq r$) outputs the second maximum value $Z_b$.

(1). While the threshold $Si(1 \leq i \leq r)$ is previously set, when $Z_a > S_a$, such a judgement is made that the reliability of recognition is high. In other words, when the maximum value among the output values of the respective output nodes of the output layer is greater than the threshold set to such an output node for outputting this maximum value, it is so judged that the reliability of recognition is high. It should be understood that $Z_a = Z_{h1}$.

(2). While the threshold $Ti(1 \leq i \leq r)$ is previously set, when $Z_b < T_b$, such a judgement is made that the reliability of recognition is high. In other words, when the second maximum value among the output values of the respective output nodes of the output layer is smaller than the threshold set to such an output node for outputting this second maximum value, it is so judged that the reliability of recognition is high. It should be understood that $Z_b = Z_{h2}$.

(3). While the threshold $U_i(1 \leq i \leq r)$ is previously set, when $(Z_a - Z_b) > U_a$, such a judgement is made that the reliability of recognition is high. In other words, when a difference between the maximum value and the second maximum value among the output values of the respective output nodes of the output layer is greater than the threshold set to such an output node for outputting this maximum value, it is so judged that the reliability of recognition is high. It should be understood that $Z_a=Z_{h1}$, and $Z_b=Z_{h2}$.

(4). While the threshold $Vi(1 \leq i \leq r)$ is previously set, when R calculated from the formula (3) can satisfy $R>V_a$, it is so judged that the reliability of recognition is high. It should be noted that in the formula (3), $Z_{h1}=Z_a$, and the summation "Σ" is carried out from i=1 to i=r. In other words, when the ratio of the maximum among the output values of the respective output nodes of the output layer to a summation of the output values of the respective output nodes is greater than the threshold set to such an output node for outputting this maximum value, it is so judged that the reliability of recognition is high.

$$R=Z_{h1}/\{\Sigma Z_i\} \qquad (3)$$

(5). While the threshold $Wi(1 \leq i \leq r)$ is previously set, when Q calculated from the formula (4) can satisfy $Q<W_a$, it is so judged that the reliability of recognition is high. It should be noted that in the formula (4), $Z_{h1}=Z_a$, and the summation "Σ" is carried out from i=2 to i=r. In other words, when Q is smaller than the threshold set to such an output node for outputting this maximum value among the output values of the output nodes of the output layer, it is so judged that the reliability of recognition is high.

$$Q=(Z_{h1}-1)^2+\Sigma(Z_{hi})^2 \qquad (4).$$

In this case, the calculated Q is equal to a squared value of the Euclidean distance (squared summation of differences of the respective components) between the ideal output vector ($Z_a=1$, $Z_i=0$, i≠a) and the actual output vector when it is assumed that a combination of the output values of the neural network 650 for recognition is recognized as a vector.

(6). A plurality of the above-described conditions (1) to (5) are selected, and only when it is judged that the reliability is high as to all of these selected conditions, the output value of the neural network 650 for recognition is transferred to the output conversion unit 690. For example, when the conditions (1) and (3) are employed, while the threshold values Si and $Ui(1 \leq i<r)$ are previously set, if $Z_a>S_a$ and also $(Z_a-Z_b)>U_a$, then it is so judged that the reliability of recognition is high. In other words, the operator arbitrarily selects the plural conditions from the above-explained conditions (1) to (5), and only when such a judgement is made that the reliability if high under all of these selected conditions, it is so judged that the reliability of recognition is high.

(7) Alternatively, as the means for evaluating the reliability of recognition, another neural network for evaluating reliability different from the above-described neural network 650 may be utilized. At this time, a connection relationship between the neural network 650 and another neural network 661 for reliability evaluation is shown in FIG. 5. The reliability evaluating neural network used at this time owns an input node for inputting the output value $Zi(1 \leq i \leq r)$ of the neural network 650, and (r+1) pieces of output nodes. It is now assumed that "r" pieces of output nodes correspond to the respective classes (classification items), and the remaining one node is used to indicate "classification impossible", and then when there is high probability in erroneous classification, a large value is outputted. The reliability evaluating neural network 661 executes learning as follows. That is, it is assumed that feature parameters of various test patterns (alternatively, patterns used in learning of neural network 650 may be employed) are inputted to the neural network 650 after the learning, and an output value at this time is used as an input of the reliability evaluating neural network 661. Then, when the recognition performed by the neural network 650 is correct, such target output that the output node corresponding to this class (classification item) becomes 1 and other output nodes become 0 is supplied to the reliability evaluating neural network. And when the recognition performed by the neural network 650 is incorrect, such desired output that the output node representing "classification impossible" becomes 1 and other output nodes become 0 is supplied to the reliability evaluating neural network.

When the actual recognition is carried out, the feature parameter of the subject image is entered into the neural network 650, and the output values of the respective output nodes thereof are inputted to the reliability evaluating neural network 661. In the case that the node for outputting the maximum value among the respective output values is the node other than the "classification impossible" node, it is so judged that the reliability of recognition is high. In other words, when the node for outputting the maximum value among the respective output values corresponds to the "classification impossible" node, it is so judged that the reliability of recognition is low. Although the number of output nodes of the reliability evaluating neural network is selected to be (r+1) in this case, the number of output nodes may be selected to be smaller than (r+1) as long as these output nodes own such a node for judging "classification impossible".

When the methods (1) to (6) are used, the thresholds having the different values are used with respect to each of the measurement modes, and these threshold values are stored in the memory 665 for reliability thresholds. Alternatively, the different methods may be utilized in the respective measurement modes.

In the output conversion unit 690, the respective output nodes are related to the output items, and the classified result is transferred to the count unit 670 and the storage memory 800. In this system, assuming that the number of output nodes of the neural network 650 for recognition is selected to be "r", and also the number of items to be actually classified by the system is selected to be "t", r≧t. In other words, when the classified result is outputted, "r" pieces of output nodes of the neural network 650 for recognition are related to the number of classification items (classes). This relating method is stored in a conversion table 695. In the output conversion unit 690, the output node of the neural network 650 for recognition supplying the maximum output value is related to the classification item, while referring to the content of the conversion table 695. When the output node where the corresponding classification item is not described in the conversion table 695 outputs the maximum value among the output nodes of the neural network 650 for recognition, no classification is carried out, which is equally handled in the case that the reliability of recognition is low. The content of this conversion table 695 can be rewritten by employing, for example, the keyboard 930 of the review equipment 900. Plural sorts of conversion tables are prepared, and hen the different conversion tables as to the respective measurement modes are selected. The reason why such an operation is performed is that there are different methods for classifying the urinary sediment, depending on the hospitals. That is, in the neural network 650 for recognition, the items are classified with precise classifications, whereas in the output conversion unit 690, some of the classification classes of the neural network 650 for recognition are combined to establish a single item, so that the classification suitable for the classification methods by the respective hospitals may be carried out. In this case, since the content of the conversion table 695 is rewritable, the classification items for the respective hospitals can be easily changed.

A count unit 670 has counters whose number is equal to that of classes (classification items) to be classified, and increments the value of the counter corresponding to the item classified in the output conversion unit 690. When the measurement as to one sample under examination is accomplished, the content of the counter is transferred to the output device 700, and the values of the respective counters are reset to "0". Every time the measurement as to one sample under examination is complete, the output device 700 outputs how many the sediment components of each of the class items could be detected. With respect to this sample under examination, the quantity of subjects which have been detected, but have not been classified is stored in the storage memory 800, e.g., the quantity of subjects which have been rejected as to their sizes, and the number of subjects which have been excluded from the classification due to low reliability. In other words, the number of recognition subjects (patterns) which have been detected, but have not been classified, whereby the recognized result thereof could not be obtained, is stored in the storage memory.

Figure 1:
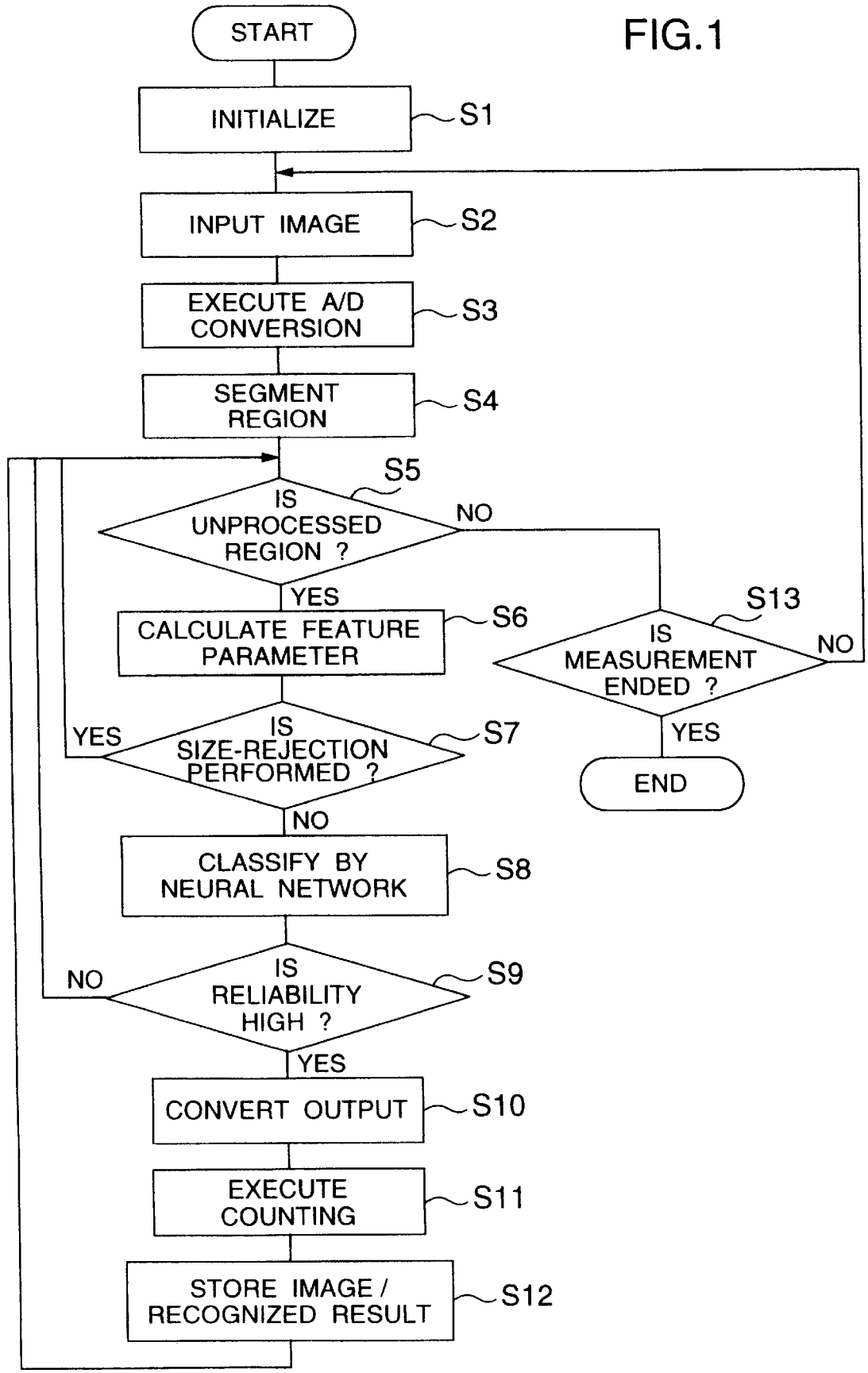
FIG. 1 is a flow chart for representing a process operation executed in a urinary sediment analyzer corresponding to a pattern recognition system according to an embodiment of the present invention.

FIG. 1 is a flow chart for representing the above-described process operations executed in the urinary sediment analyzer corresponding to the pattern recognition system according to one embodiment of the present invention. That is, FIG. 1 shows the process flow operation as to one object under examination A description will now be made of this process flow operation:

(step S1): As the initialization purpose, clear the counters of the count unit 670 (reset), select the size rejection method, set the size rejecting threshold to the memory 645 for rejection thresholds, set the reliability evaluating means, set the reliability evaluating threshold to the memory 665 for reliability thresholds, and set the output conversion table 695.

(step S2): Photograph the subject image to enter the photographed image.

(step S3): A/D-convert the image signal (step S4): Perform the region segmentation for segmenting the image signal into the subject region and the background region.

(step S5): Check as to whether or not the unprocessed subject region is present, since there are some cases that a plurality of independent subjects (regions) exist in a single image. When there is no unprocessed subject region, execute a process operation defined at a step S13. When there is an unprocessed subject region, execute process operations defined at steps subsequent to the step S6.

(step S6): Calculate the image feature parameter of the subject region of interest.

(step S7): Reject such a subject having a size smaller than a predetermined size by employing the amounts indicative of the dimension of the subject region, e.g., the area, the perimeter, and the projection length among the image feature parameters. When the rejection is carried out, the process operation is returned to the step S5 at which the process operation for the remaining subject region contained in the image is carried out. When the size rejection is not performed, the process operation defined at a step S8 is executed.

(step S8): Input the feature parameter into the neural network 650 for recognition so as to be classified.

(step S9): Judge as to whether or not the reliability of classification is high with reference to the output values of the neural network 650 for recognition. The judgement as to whether or not the reliability of classification is high is performed by employing any one of the above-described methods (1) to (7). When it is so judged that the reliability is low, the process operation defined at the step S5 is carried out, at which the remaining subject regions contained in the image are processed When it is so judged that the reliability is high, a process operation defined at a step S10 is carried out.

(step S10): Execute the output conversion by which the respective output nodes of the neural network 650 for recognition are related to the respective classification items.

(step S11): Count how many subjects of the respective classification items are detected by the count unit 670.

(step S12): Both the subject image and the recognized result are stored in the storage memory 800. After the process operations up to the step S12 are complete, the process operation is again returned to the step S5, at which the process operation for the remaining subject regions contained in the image is carried out.

(step S13): Judge as to whether or not the measurement for this sample under examination is accomplished. When the measurement is accomplished, the process operation is ended. Conversely, when the measurement is not accomplished, the process operation is returned to the step S2, at which the image is newly inputted, and then the process operations for the above-described steps are performed.

While the urinary sediment analyzer has been described as the embodiment mode of the pattern recognition system according to the present invention, the present invention is not limited thereto, but may be applied to various blood image classifications, for example, red blood cell classifications and white blood cell classifications. Apparently, the present invention may be applied to such systems capable of classifying an outer shape of a plane, an outer shape of a leaf of a plant, and a shape of micro-organism.

In pattern recognition systems, although subjects which appear frequently may be allowed to be more or less rejected, it is required that subjects which rarely appear must not be overlooked. In other words, with respect to the subjects which appear frequently, these subjects may be more or less rejected. To the contrary, as to the subjects which rarely appear, the quantity of those which are rejected should be made as small as possible. In particular, with respect to the urinary sediment examination, as previously explained, it is effective that while the thresholds are set to the output values of the respective output nodes of the neural network, the recognized result are rejected. For instance, the following fact could be found out in the urinary sediment examination as to the appearing subjects. That is, as a result of comparison between the coincident rate by the method for performing no rejection of the recognized result and the coincident rate by the above-explained method (1) for performing the rejection of the recognized result, the first-mentioned coincident rate was approximately 60% and the second-mentioned coincident rate was approximately 90%. This comparison was carried out as to the same object under examination. The coincident rate implies such a rate that the classified result obtained by the analyzer system and the classified result obtained by the observation are the same among all subjects. As a consequence, the classified result obtained by the analyzer system was approximated to the classified result obtained by the observation.

What is claimed is:

1. A pattern recognition system comprising:

pattern recognition processing means having a network structure constructed of an input layer for inputting feature parameters of a subject under recognition as input information, a hidden layer for processing said input information and an output layer for outputting a processed result, said pattern recognition processing means comparing output values of respective output nodes for constituting said output layer, corresponding to said input information, with each other;

storage means for storing a classification item corresponding to said output node whose output value is maximum, as a recognized result with respect to said input information;

reliability evaluating means for setting a reliability threshold value with respect to an output value of each of said output nodes and for evaluating reliability of said recognized result based upon the output value of each of said output nodes and said reliability threshold value with respect to the output value of each of said output nodes; and memory which stores said reliability threshold values;

wherein, when said reliability evaluating means judges that the reliability is high, said recognized result is stored into said storage means.

2. A pattern recognition system as claimed in claim 1 wherein when a second maximum value among the output values of said respective output nodes is smaller than said reliability threshold value with respect to said output node for outputting said second maximum value, said reliability evaluating means judges that the reliability is high.

3. A pattern recognition system as claimed in claim 1 wherein when a difference between a maximum value and a second maximum value among the output values of said respective output nodes is greater than said reliability threshold value with respect to the output node for outputting said maximum value, said reliability evaluating means judges that the reliability is high.

4. A pattern recognition system as claimed in claim 1 wherein said reliability evaluating means calculates a difference between an output value of each of said output nodes and another output value when it is assumed that said reliability evaluating means could obtain an ideal recognized result as to each of said respective output nodes and judges that the reliability is high when a squared summation of said difference is smaller than said reliability threshold value with respect to said output node for outputting a maximum value.

5. A pattern recognition system as claimed in claim 1 wherein:

if a plurality of conditions selected from the below-mentioned conditions (1) to (5) are fully satisfied, then said reliability evaluating means judges that the reliability is high:

(1) when a maximum value among the output values of said respective output nodes is greater than said reliability threshold value with respect to said output node for outputting said maximum value;

(2) when a second maximum value among the output values of said respective output nodes is smaller than said reliability threshold value with respect to said output nods for outputting said second maximum value;

(3) when a difference between a maximum value and a second maximum value among the output values of said respective output nodes is greater than said reliability threshold value with respect to the output node for outputting said maximum value;

(4) when a ratio of a maximum value among the output values of the respective output nodes to a summation of the output values of the respective output nodes is greater than said reliability threshold value with respect to the output node for outputting said maximum value; and (5) when said reliability evaluating means calculates a difference between an output value of each of said output nodes and another output value when it is assumed that said reliability evaluating means could obtain an ideal recognized result as to each of said respective output nodes, a squared summation of said difference is smaller than said reliability threshold value with respect to said output node for outputting a maximum value.

6. A pattern recognition system as claimed in claim 5 wherein an operator can select a plurality of combined conditions.

7. A pattern recognition system according to claim 1, wherein the subject under recognition are solid components contained in urine, an image of the solid components is photographed as a still image obtained by an imaging system of a urinary sediment analyzer comprising a flow cell, a pulse lamp, and an optical enlarging means, and wherein urine sample fluid containing the solid components flows into said flow call, light emitted from said pulse lamp irradiate to the solid components passing through a photographing region within said flow call, said still image is obtained, by employing said optical enlarging means, as an enlarged image of the solid components.

8. A pattern recognition system comprising:

pattern recognition processing means having a network structure constructed of an input layer for inputting feature parameters of a subject under recognition as input information, a hidden layer for processing said input information, and an output layer for outputting a processed result, said pattern recognition processing means comparing output values of respective output nodes for constituting said output layer, corresponding to said input information, with each other;

storage means for storing a classification item corresponding to said output node whose output value is maximum, as a recognized result with respect to said input information;

reliability evaluating means for setting a reliability threshold value with respect to an output value of each of said output nodes and for evaluating reliability of said recognized result based upon the output value of each of said output nodes and said reliability threshold value with respect to the output value of each of said output nodes; and memory which stores said reliability threshold values;

wherein, when a maximum value among the output values of said respective output nodes is greater than said reliability threshold value with respect to said output node for outputting said maximum value said reliability evaluating means judges that the reliability is high; and wherein, when said reliability evaluating means judges that the reliability is high, said recognized result is stored into said storage means.

9. A pattern recognition system as claimed in claim 8 wherein an operator can set said reliability threshold value.

10. A pattern recognition system comprising:

pattern recognition processing means having a network structure constructed of an input layer for inputting feature parameters of a subject under recognition as input information, a hidden layer for processing said input information, and an output layer for outputting a processed result, said pattern recognition processing means comparing output values of respective output nodes for constituting said output layer, corresponding to said input information, with each other;

storage means for storing a classification item corresponding to said output node whose output value is maximum, as a recognized result with respect to said input information;

reliability evaluating means for setting a reliability threshold value with respect to an output value of each of said output nodes and for evaluating reliability of said recognized result based upon the output value of each of said output nodes and said reliability threshold value with respect to the output value of each of said output nodes; and memory which stores said reliability threshold values;

wherein, when a ratio of a maximum value among the output values of the respective output nodes to a summation of the output values of the respective output nodes is greater than said reliability threshold value with respect to the output node for outputting said maximum value, said reliability evaluating means judges that the reliability is high; and wherein, when said reliability evaluating means judges that the reliability is high, said recognized result is stored into said storage means.

11. A pattern recognition system comprising:

pattern recognition processing means having a network structure constructed of an input layer for inputting feature parameters of a subject under recognition as input information a hidden layer for processing said input information, and an output layer for outputting a processed result, said pattern recognition processing means comparing output values of respective output nodes for constituting said output layer, corresponding to said input information, with each other;

storage means for storing a classification item corresponding to said output node whose output value is maximum, as a recognized result with respect to said input information;

reliability evaluating means for setting a reliability threshold value with respect to an output value of each of said output nodes and for evaluating reliability of said recognized result based upon the output value of each of said output nodes and said reliability threshold value with respect to the output value of each of said output nodes;

memory which stores said reliability threshold values;

output conversion unit which relates each of said output nodes to output classification items using a conversion table relating each of said output nodes to output classification items;

wherein, when said reliability evaluating means judges that the reliability is high, said recognized result is stored into said storage means.

* * * * *